United States Patent [19]
Macho et al.

[11] Patent Number: 5,096,836
[45] Date of Patent: Mar. 17, 1992

[54] DIAGNOSTIC TEST CARRIER

[75] Inventors: Heinz K. Macho, Fürth/Fahrenbach; Klaus D. Hungenberg, Birkenau-Hornbach; Norbert Becker, Lampertheim, all of Fed. Rep. of Germany

[73] Assignee: Boehringer Mannheim GMBH, Mannheim, Fed. Rep. of Germany

[21] Appl. No.: 587,168

[22] Filed: Sep. 19, 1990

Related U.S. Application Data

[63] Continuation of Ser. No. 205,460, Jun. 10, 1988, abandoned.

[30] Foreign Application Priority Data

Jun. 27, 1987 [DE] Fed. Rep. of Germany ....... 3721237

[51] Int. Cl.$^5$ ............................................. G01N 31/22
[52] U.S. Cl. ........................................ 436/169; 422/56; 422/57; 422/58
[58] Field of Search ....................... 422/56-58; 436/169, 170; 427/2; 156/167, 291, 295

[56] References Cited
U.S. PATENT DOCUMENTS 4,582,684  4/1986  Vogel et al. .................... 422/57

FOREIGN PATENT DOCUMENTS 0166365  1/1986  European Pat. Off. .
0287883  10/1988  European Pat. Off. .......... 422/57

*Primary Examiner*—Jill Johnston
*Attorney, Agent, or Firm*—Felfe & Lynch

[57] ABSTRACT

At least two layers are fixed together at a distance so that a gap is present between them, wherein the layers are connected with one another by a plurality of discrete melt adhesive regions, intermediate spaces being present between the melt adhesive regions so that a liquid transport in the gap between the layers is assured through the intermediate spaces. To produce this test carrier, the melt adhesive in the form of discrete regions, between which intermediate spaces are present, is applied to a first layer material in a thickness which is greater than the desired gap and a second layer material is pressed against the melt adhesive regions while the melt adhesive is still sufficiently hot in order to be bindable in such a manner that it binds with the melt adhesive but a gap remains between the layer materials.

9 Claims, 3 Drawing Sheets

DIAGNOSTIC TEST CARRIER

This application is a continuation of application Ser. No. 205,460, filed June 10, 1988, and now abandoned.

BACKGROUND OF THE INVENTION

The present invention is concerned with a diagnostic test carrier with at least two layers which are fixed at a distance from one another so that there is a gap present between them and is also concerned with a process for the production of such a test carrier.

For the qualitative or quantitative analytical determination of components in body fluids, especially in blood, so-called carrier-bound tests have recently been used to an increasing extent. In these, reagents are embedded into appropriate layers of a solid carrier which is brought into contact with the sample. The reaction of the sample and reagents results in a detectable signal, especially a color change, which can be evaluated visually or with the help of an apparatus, usually by reflection photometry.

Test carriers are frequently constructed as test strips which consist essentially of a longitudinal support layer of synthetic resin material with test fields applied thereon. However, test carriers are also known which are made as square or rectangular platelets.

Test carriers of the initially described kind are known, for example, from Research Disclosure, Vol. 200, Abstract No. 22, pp. 554-557/1980 (in the following referred to as RD). The layers are there referred to as support member and as cover member. Both parts are planar sheets made of a solid synthetic resin material. For the production of a gap between the parts, a liquid-impermeable intermediate disc is placed on their circumference. The parts are connected, for example, by conventional adhesives or by ultrasonic welding.

A similar test carrier construction is described in U.S. Pat. No. 4,426,451.

From Federal Republic of Germany Patent Specification No. 26 41 097 and from U.S. Pat. No. 4,088,448, there is known a test carrier-shaped cuvette in which a gap is present within a one-piece synthetic resin part.

In all these cases, the gap serves for the transport of a liquid in the gap with the help of capillary force. In the case of the construction of diagnostic test carriers, this is frequently a useful constructional element. Thus, for example, the gap, as described in the RD reference, serves to fill a certain hollow space of the test carrier with a sample liquid. The flow of liquid can, as described in RD, possibly also be interrupted and, on the basis of a pressure impact, again be continued.

In spite of these advantages, the gap construction for test carriers has not been used hitherto to any great extent, the reason for which may well be that the previously known test carriers of this kind are laborious to produce.

SUMMARY OF THE INVENTION

Therefore, it is an object of the present invention to provide a diagnostic test carrier and a process for the production thereof in which a gap is present between two layers of a test carrier making possible a liquid transport, the test carrier thereby being simple and economic to produce in large numbers.

Thus, according to the present invention, there is provided a diagnostic test carrier with at least two layers which are fixed together at a distance so that a gap is present between them, wherein the layers are connected with one another by a plurality of discrete melt adhesive regions, intermediate spaces being present between the melt adhesive regions so that a liquid transport in the gap between the layers is possible through the intermediate spaces.

The present invention also provides a process for the production of this test carrier, wherein the melt adhesive in the form of discrete regions, between which intermediate spaces are present, is applied to a first layer material in a thickness which is greater than the desired gap and a second layer material is pressed against the melt adhesive regions while the melt adhesive is still sufficiently hot in order to be bindable in such a manner that it binds with the melt adhesive but a gap remains between the layer materials.

The layers bound by the melt adhesive regions can consist of practically all materials which are usually employed for the production of multi-layer test carriers. In particular, there can be used non-absorbent materials and mainly synthetic resin films. However, there can also be used layers of absorbent materials, for example papers, fleece, fabrics, textiles or porous synthetic resin materials as layer materials. Preferably, however, at least one of the layers which border the gap consists of a non-absorbent material.

As melt adhesives, there can be used commercially-available products, for example those based on ethylenevinyl acetate co-polymers, polyesters or polyamides. Such melt adhesives have already been used for the production of diagnostic test carriers, in which case, however, they are usually applied full-facedly on to the layer to be bound and the other layer is then pressed against the melt adhesive surface.

In the case of another known process, a strip of melt adhesive material is used in order to bind one or more test carrier layers on their edges to a substrate.

Surprisingly, in the scope of the present invention, we have found that a reproducible and uniform gap (especially for the purpose of liquid transport) can be formed on a test carrier when the melt adhesive is not applied full-facedly but rather merely in regions on to a layer material to be bound, the thickness of the melt adhesive application thereby being greater than the desired gap width and the second layer material is not firmly pressed thereagainst with the help of appropriate measures, which are explained hereinafter in greater detail, but rather only so pressed on that a gap remains corresponding to the desired gap width.

At the time of the pressing on, the melt adhesive must be sufficiently hot that it binds with the second layer material. This is preferably achieved by applying the second material shortly after the melt adhesive application and thus during the so-called "open time" of the melt adhesive. In exceptional cases, for example when the first layer, after application of the melt adhesive regions, is to be coated with a wetting agent, it may be desirable to allow the melt adhesive to solidify after the application of the regions and to heat the adhesive again before application of the second material.

The melt adhesive regions can have greatly varying forms. They must, in any case, be such that sufficiently large intermediate spaces remain to enable liquid transport between them. Preferably, they cover from 10 to 70% and most preferably from 15 to 50% of the total connecting surface of the layers.

DETAILED DESCRIPTION OF PREFERRED EMBODIMENTS

Figure 1:
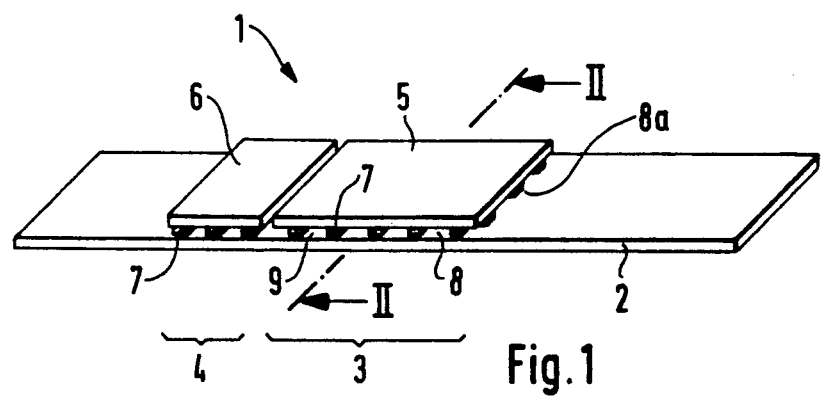
FIG. 1 is a perspective view of a test carrier according to the present invention.
Figure 2:
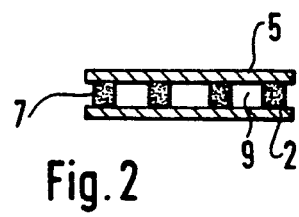
FIG. 2 is a cross-section through the test carrier according to FIG. 1 along the line II—II.

The test carrier 1 illustrated in FIGS. 1 and 2 has a support layer 2 on which, directly next to one another, a liquid transport zone 3 and a detection zone 4 are arranged. In the region of the liquid transport zone 3 a non-absorbent covering layer 5 is fixed and an absorbent detection layer 6 is fixed in the region of the detection zone 4. Both layers 5 and 6 are fixed by means of melt adhesive regions 7 on the support layer 2, in such a manner that a gap 8 is present between the support layer 2 and the layers 5 and 6, respectively.

In the gap 8, a sample liquid can be transported by capillary force. If, for example, it is applied to the end 8a of the gap 8 facing away from the detection zone 4, then it first spreads out between the covering layer 5 and the carrier layer 2 in the region of the liquid transport zone 3, flowing through the intermediate spaces 9 between the melt adhesive regions, which can better be seen in FIG. 2. Due to the binding of the two non-absorbent materials with a gap lying therebetween, one produces, in a simple way, a liquid transport path. This configuration produces a device which possesses the ability to achieve the desired spreading out of the sample. The device is not dependent upon batch variations in the material used in its construction, such as variations in capillary active liquid transport layers made of fleeces and fabrics. Uniformity is achieved even in large scale production.

When a further supply of liquid is added, the sample liquid also gets into the gap between detection layer 6 and support layer 2 in the detection region 4. It thereby wets the detection layer 6 on its underside so that the sample liquid penetrates into the absorbent detection layer 6 and can react with reagents present therein. This can, for example, result in a color change characteristic for the desired analytical determination. By means of the connection according to the present invention of a non-absorbent layer with an absorbent layer, one transports the sample first in the layer direction for the distribution of the sample liquid, and then obtains subsequent penetration of the sample into the absorbent layer.

Details of reagent compositions and of methods of analysis are not the subject of the present invention. Indeed, a plurality of known test carrier reactions can be used.

A test carrier with the construction according to the present invention of two adjacent layers separated from one another by a gap can also be constructed in greatly differing ways. Consequently, FIG. 1 is only to be understood as being an example for a possible use. The illustrated test carrier can be adapted by means of known supplementary elements to the particularly desired course of the test.

Thus, for example, on the end 8a of the capillary gap 8 there can simply be applied a drop of blood which is then sucked up into the capillary gap. However, other test carrier layers can also be placed before the end 8a through which the sample passes into the capillary gap 8. Such other layers may contain reagents for a prereaction.

In all, it is clear that a capillary gap present between two test carrier layers, through which a sample liquid can flow, can be used in many ways in test carrier technology.

Figure 3:
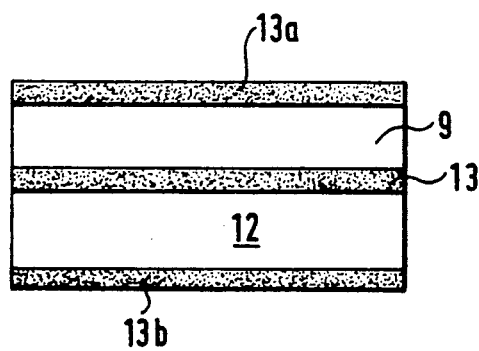
FIG. 3 is a view of a piece of layer material with melt adhesive regions in the form of strips.
Figure 4:
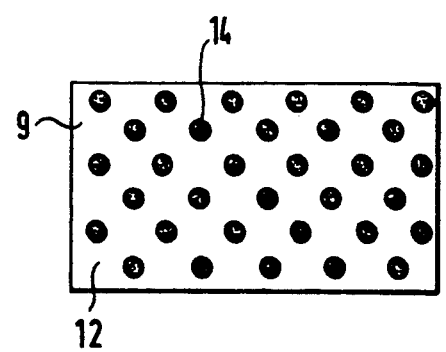
FIG. 4 is a view corresponding to FIG. 3 with melt adhesive regions in the form of round particles.

FIGS. 3 and 4, by way of example, two different possible forms of the melt adhesive regions.

In FIG. 3, the melt adhesive regions applied to the layer material 12 have the shape of strips 13. They can, as illustrated, run in the longitudinal direction of a test carrier. It can thereby be desirable that at least a part of the strips 13a and 13b are arranged near the edges of the layers to be stuck together so that the hollow space lying therebetween is closed off on the side of the test carrier.

Insofar as such strip-shaped melt adhesive regions are used, it is necessary that the intermediate spaces 9 run in the desired direction of flow of the sample liquid to be transported. Furthermore, care must be taken for a relatively exact arrangement of the melt adhesive strips 13 on the layer material 12.

Surprisingly, we have found that very good results are achieved when the melt adhesive is applied to the first layer material in the form of particles, thus for example in the form of round, quadratic or rectangular dots. In FIG. 4, for example, round dots 14 are illustrated. In the case of such a melt adhesive application, no special adjustment measures are necessary. Nevertheless, a problem-free liquid transport is achieved. This applies even when, in strip-shaped test carrier, a comparatively large liquid transport path is to be provided, such as, for example, in the case of the test carriers described in Federal Republic of Germany Patent Application No. 36 43 516, which corresponds to U.S. application Ser. No. 134,950, filed Dec. 18, 1987 to which reference is made. Although the side edges of the liquid transport path in the case of particle-shaped melt adhesive application remain open, dependable and complete liquid transport is achieved. This is all the more surprising since the polymers used for the melt adhesive are hydrophilic.

In order to ensure a gap distance which is as uniform as possible between the two layers bound by the melt adhesive regions, the melt adhesive regions are preferably of equal size and distributed uniformly over the whole of the connecting surface. However, in special cases, it can be desirable to deviate from this rule. If, for example, it is necessary to carry out an optical evaluation of the liquid present between the layers in a test carrier, at least one of the layers must be transparent.

In this case, melt adhesive particles could disturb an optical evaluation in the intended region. Practical experiments have shown that a uniform distance between the layers can also still be achieved when, because of such requirements, the melt adhesive regions cannot be uniformly distributed. In this case, it is preferable to use layer materials which have a sufficient stiffness.

The melt adhesive particles preferably have an average surface area of from 0.03 to 5.0 mm$^2$, the upper limit preferably being 0.1 mm$^2$.

The thickness of the melt adhesive regions, which determines the vertical dimension of the gap, is preferably from 0.02 to 1.0 mm, and especially preferably from 0.02 to 0.3 mm. If these preferred values are maintained, there are obtained especially advantageous liquid transport properties.

Figure 5:
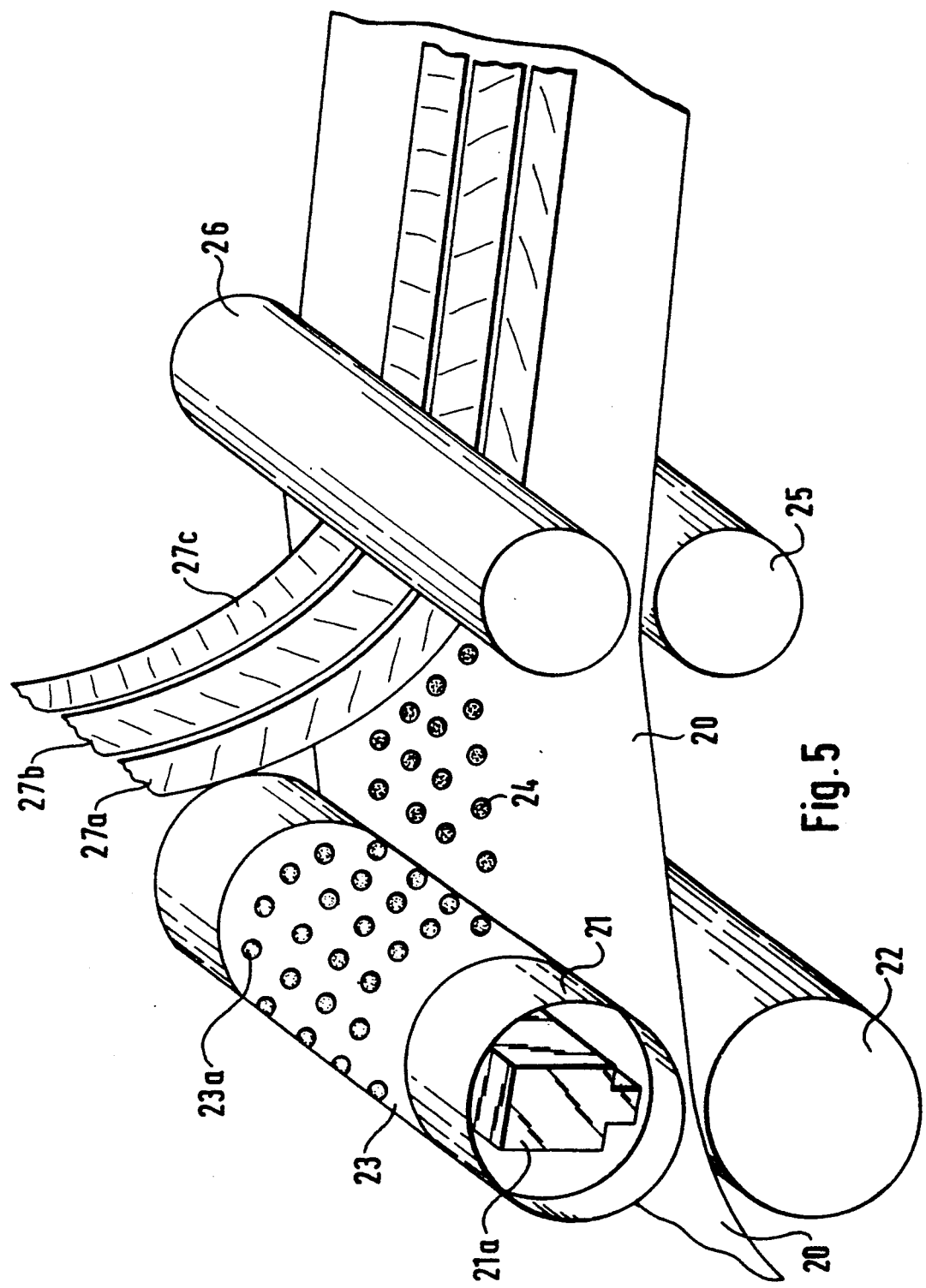
FIG. 5 is an illustration in principle of a production process with the help of screen printing.

FIG. 5 shows a schematic, perspective view of a production process according to the present invention in which the melt adhesive regions are applied by a screen printing process.

A first layer material 20 is first transported between a perforated roller 21 and a coating roller 22, which is preferably heatable or coolable. The melt adhesive is pressed by means of a wide slot nozzle 21a through the holes 23a of the sieve 23, the shape of the melt adhesive particles 24 thereby produced being determined by the shape of the holes 23a of the sieve 23.

The layer material 20 with the melt adhesive particles 24 is further transported through a slot between a lower pressure roller 25 and an upper pressure roller 26. To the same gap are supplied, in the illustrated embodiment, three strips 27a, 27b and 27c of a second layer material. Thus different second layer materials can also be connected in one working step with the first layer material. It can be advantageous to provide the second layer material, on the side facing the first layer material, with a layer containing a wetting agent.

It is important for the present invention that the second layer material 27a, 27b, 27c is not so firmly pressed together by the rollers 25 and 26 that no gap remains any longer between the layer materials or that the melt adhesive particles 24 are so strongly pressed out that the intermediate spaces present between them disappear and thus a continuous melt adhesive layer results. On the contrary, the pressing on must take place in such a manner that a definite and reproducible distance remains between the layer materials.

This is preferably achieved by adjusting the pressing-on rollers 25 and 26 to a fixed distance. However, it can also be preferable so to adjust the pressing-on force between the rollers 25 and 26 that, having regard to the material properties of the layer materials and of the viscosity of the layer particles 24, the desired distance is achieved.

The transport speed of the layer material 20 and the distance between the perforated roller 21 and the pressing-on rollers 25 and 26 determine the period of time between the application of the melt adhesive and the pressing on of the second layer material. It is important that this time is such that the melt adhesive is still sufficiently hot in order to retain its ability to bind, whereas, on the other hand, it has preferably cooled to such an extent that it has a relatively high viscosity which gives the melt adhesive particles 24 a sufficient stability.

Figure 6:
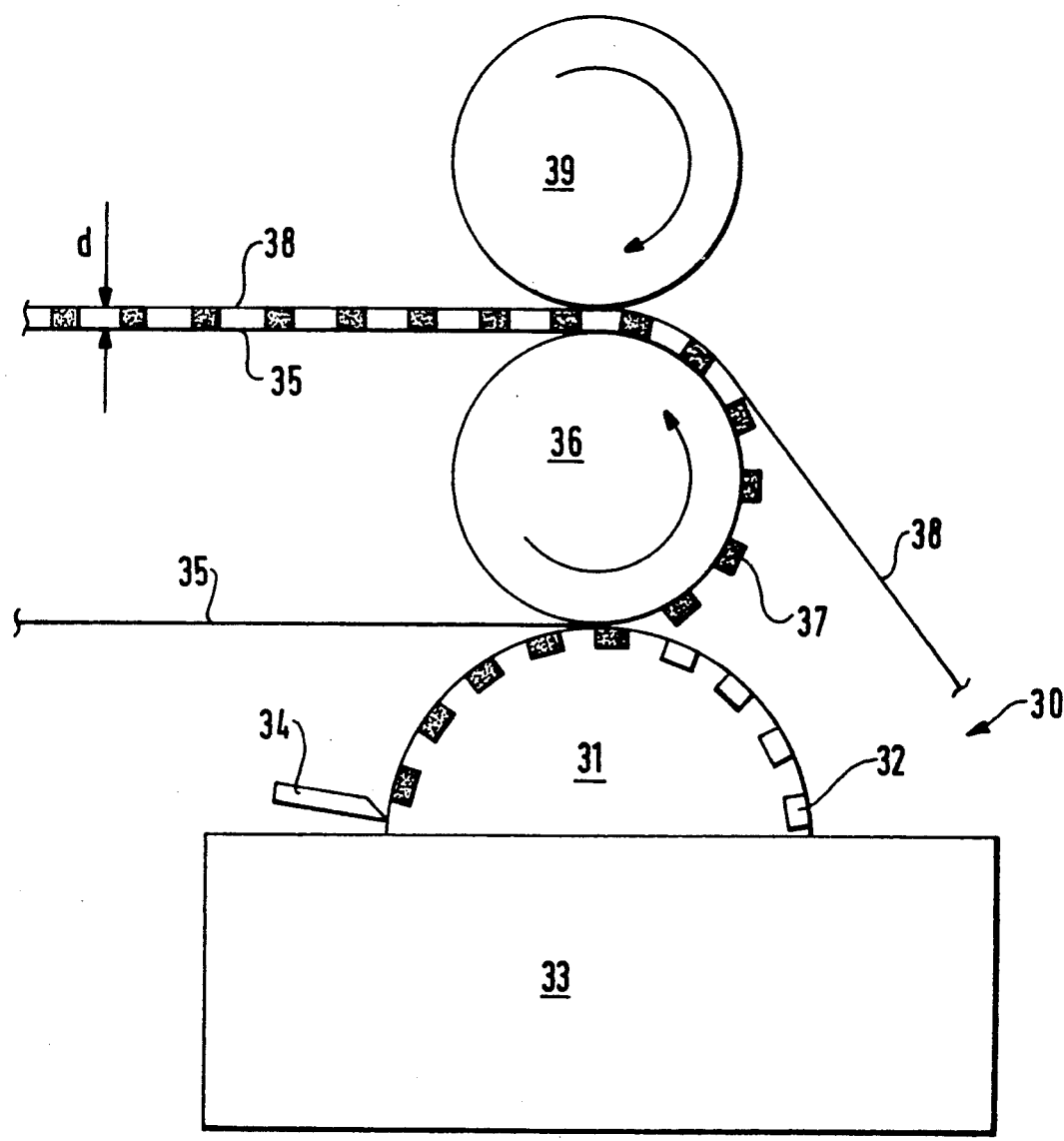
FIG. 6 is an illustration in principle of a production process with wheel application.

FIG. 6 illustrates another possibility for applying the melt adhesive regions, namely a wheel application device 30.

Its application wheel 31 has, on its surface, a plurality of depressions 32 which correspond in cross-section and depth to the desired melt adhesive regions. They are filled with melt adhesive by rotating the wheel 31 in a container 33 filled with melt adhesive, excess of melt adhesive thereby being wiped off by a doctor blade 34.

A first carrier material 35 is passed through between the application wheel 31 and a deflection roller 36, melt adhesive particles 37 thereby being applied. The second layer material 38 is pressed by the pressure roller 39, analogously to the embodiment illustrated in FIG. 5, against the melt adhesive particles 37 so that a distance indicated in FIG. 6 by d remains between the layers of the final composite material.

The second layer material is introduced obliquely from below in such a manner that it partly wraps round the deflection roller 36. In this way, an especially good connection is achieved. The pressing-on force and thus the size of the distance d in the case of a given melt adhesive application thickness can, in this case, also be controlled by the tension under which the second layer material 38 is introduced and removed.

A more detailed description of the application process is not necessary since the application of melt adhesives not only by a screen printing process but also by a wheel application is known for other purposes of use.

The following Examples are given for the purpose of illustrating the present invention.

EXAMPLE 1

Connecting of non-absorbent materials

With a wheel application according to FIG. 6, EVA (ethylene vinyl acetate) melt adhesive of the type Jet-Melt 3764 of the 3M Company was applied at a temperature of 170° C., the melt adhesive particles thereby having a surface area of 1.1 × 0.5 mm. Pressing on takes place via a pressure roller which is heated to 70° C., a fixed gap between the layers to be connected of 70u width thereby being adjusted.

The first layer, on to which the melt adhesive particles are applied, is a polyethylene terephthalate film of 0.35 mm thickness. With the help of the melt adhesive particles, it is connected with a polycarbonate film of 0.25 mm thickness.

The melt adhesive particles are uniformly applied with such a density that, in all, about 26% of the connecting surface is covered with melt adhesive.

The composite layer so obtained is outstandingly useful as a capillary transport path within the construction of a test carrier. For example, a sample section of 30 mm length and 5 mm breadth fills uniformly within 10 seconds with a marlon-containing glucose solution used for experimental purposes, about 15 μl of liquid thereby being taken up.

EXAMPLE 2

If, instead of the polycarbonate film used in Example 1, there is used a gel-bond film of the FMC Corporation, then there is obtained a quicker filling rate of the capillary gap. It is filled with marlon-containing glucose solution in about 4 seconds and with blood the filling time is about 25 seconds.

EXAMPLE 3

Connecting of an absorbent and of a non-absorbent material

With a wheel application device, a polystyrene film is connected with a multifilar polyester fabric which carries a reagent coating.

The melt adhesive particles applied have a diameter of about 0.4 mm to 0.5 mm and cover about 55% of the connecting surface.

There is used an EVA melt adhesive of the type Jet-Melt 3764 of the 3M Company, which is applied at an application temperature of 150° C., the pressure roller being heated to a temperature of 40° C.

In the case of this Example, the breadth of the capillary gap is varied by varying the pressing-on force with which the two layers are pressed against one another.

For a sample surface of about 10 × 6 mm, there are obtained the following results: in the case of a pressing-on force of 0.4 bar, the gap fills in 6.5 seconds with a total of about 9 mg of blood; in the case of a pressing-on force of 0.5 bar, the gap fills in 9.5 seconds with about 8.2 mg of blood; in the case of a pressing-on force of 0.8 bar, the gap fills in 13 seconds with about 6.7 mg of blood.

It will be understood that the specification and examples are illustrative but not limitative of the present invention and that other embodiments within the spirit and scope of the invention will suggest themselves to those skilled in the art.

We claim:

1. A test carrier for determining analyte in a fluid sample, said test carrier comprising
    a sample application zone comprising a first layer and a second layer and a gap between said first and second layers, said first and second layers being non-absorbent,
    an evaluation zone comprising a first layer and a second layer and a gap between said first and second layer, at least one of said layers being non-absorbent,
    said first and second layers in both of said zones being connected together by a plurality of discrete melt adhesive means having a thickness, said adhesive means positioned between said first and second layers so as to provide a plurality of intermediate spaces between said first and second layers, said intermediate spaces having a vertical dimension defining said gap separating said first and second layers, said vertical dimension being defined by the thickness of the melt adhesive means, said gap being dimensioned to assure a capillary action so that said fluid sample can spread out parallel to said first and second layers in a liquid transport path,
    said liquid transport path formed by said first and second layers in said sample application and said first and second layers in said evaluation zone, said transport path being parallel to said layers and extending through both of said zones.

2. The test carrier of claim 1, wherein said adhesive means have a thickness of from 0.02 to 1.0 mm.

3. The test carrier of claim 1, wherein said adhesive means have a thickness of from 0.02 to 0.3 mm.

4. The test carrier of claim 1, wherein said adhesive means are adhesive particles.

5. The test carrier of claim 1, wherein said particles have an average surface area of from 0.03 to 5.0 mm$^2$.

6. The test carrier of claim 1, wherein said adhesive means comprise a total surface area of for 10 to 70% of the surface area of the layers connected thereby.

7. The test carrier of claim 1, wherein said adhesive means comprise a total surface area of from 15 to 50% of the surface area of the layers connected thereby.

8. Method for determining an analyte in a liquid sample comprising contacting said sample to a device of claim 1, wherein at least one of said layers contains a reagent means which produces a detectable signal in the presence of said analyte, and detecting said signal as an indication of said analyte.

9. Method of claim 8, wherein said liquid sample is whole blood.

* * * * *